United States Patent
Stone et al.

(10) Patent No.: US 9,675,786 B2
(45) Date of Patent: Jun. 13, 2017

(54) DEVICES, SYSTEMS AND METHODS FOR DIVERTING FLUID TRAPPED IN A SOLID ORGAN

(71) Applicant: University of Rochester, Rochester, NY (US)

(72) Inventors: Jonathan Stone, Rochester, NY (US); Ankur Chandra, Rochester, NY (US)

(73) Assignee: University of Rochester, Rochester, NY (US)

( * ) Notice: Subject to any disclaimer, the term of this patent is extended or adjusted under 35 U.S.C. 154(b) by 663 days.

(21) Appl. No.: 13/839,222

(22) Filed: Mar. 15, 2013

(65) Prior Publication Data

US 2014/0276342 A1     Sep. 18, 2014

(51) Int. Cl.
*A61M 27/00* (2006.01)

(52) U.S. Cl.
CPC ........ *A61M 27/006* (2013.01); *A61M 27/002* (2013.01)

(58) Field of Classification Search
CPC .............. A61M 27/002; A61M 27/006; A61M 2202/0464; A61M 2210/0693
See application file for complete search history.

(56) References Cited

U.S. PATENT DOCUMENTS

| | | | |
|---|---|---|---|
| 4,950,232 A * | 8/1990 | Ruzicka et al. | 604/43 |
| 5,954,687 A * | 9/1999 | Baudino | 604/48 |
| 6,905,474 B2 | 6/2005 | Borgesen | |
| 7,037,288 B2 | 5/2006 | Rosenberg | |
| 7,118,548 B2 | 10/2006 | Borgesen | |
| 8,088,091 B2 | 1/2012 | Thomas | |
| 2004/0082900 A1 | 4/2004 | Luttich | |
| 2005/0137579 A1 | 6/2005 | Heruth | |
| 2005/0251144 A1 * | 11/2005 | Wilson | A61B 5/031 606/108 |
| 2006/0111688 A1 * | 5/2006 | Kraus et al. | 604/415 |
| 2009/0246252 A1 * | 10/2009 | Arps et al. | 424/425 |
| 2010/0222732 A1 | 9/2010 | Sevrain | |
| 2012/0130467 A1 | 5/2012 | Selden | |

* cited by examiner

*Primary Examiner* — Jacqueline Stephens
*Assistant Examiner* — Benjamin Klein
(74) *Attorney, Agent, or Firm* — Hyman IP Law; Laurence J. Hyman

(57) ABSTRACT

The invention provides devices with specialized ends for diverting fluids trapped in an organ. In a first group of embodiments, the invention provides implantable devices that shunt fluid trapped in a patient's organ to its normal physiological destination. In a second group of embodiments, the invention provides devices with specialized ends for connecting the devices to conventional medical tubing to divert fluid trapped in an organ to a destination selected by the practitioner. The invention further provides systems and methods of using the devices.

25 Claims, 5 Drawing Sheets

DEVICES, SYSTEMS AND METHODS FOR DIVERTING FLUID TRAPPED IN A SOLID ORGAN

CROSS-REFERENCE TO RELATED APPLICATIONS

Not applicable.

STATEMENT OF FEDERAL FUNDING

Not applicable.

BACKGROUND OF THE INVENTION

Conditions trapping of fluids within an organ can create pressure within the organ leading to organ damage. For example, hydrocephalus, or "water on the brain," resulting from an over-accumulation of cerebrospinal fluid ("CSF"), can increase intracranial pressure to the extent of causing mental disability or even death. There are some 69,000 hospital admissions for this condition annually in the United States alone, followed by some 39,000 shunting procedures to shunt CSF from brain ventricles to relieve overpressure. Berlis et al., Operative Neurosurgery 59:474-480 (2006), reported the drainage of an intracranial cyst by use of a balloon-mounted vascular stent.

It would be desirable to have additional means of relieving overpressure in hydrocephalus, and other conditions in which a fluid excess in a body cavity creates an overpressure on an organ.

PARTIES TO JOINT RESEARCH AGREEMENT

Not applicable.

REFERENCE TO SEQUENCE LISTING OR TABLE SUBMITTED ON COMPACT DISC AND INCORPORATION-BY-REFERENCE OF THE MATERIAL [SPECIFY NUMBER OF DISCS AND FILES ON EACH]

Not applicable.

BRIEF SUMMARY OF THE INVENTION

The invention provides devices, systems, and methods for diverting fluid from a patient's organ to either its normal physiological destination or a destination chosen by the practitioner.

In a first group of embodiments, the invention provides implantable medical devices that provide fluid communication between two body cavities, wherein the device comprises a body and a second end protector, in which (a) the body is tubular and has a transverse axis having a diameter, is permeable or impermeable, has a first end and a second end and has a lumen fluidly connecting the first and second ends and (b) the second end protector extends from the second end of the body, has a first end joined to the second end of the body and fluidly connected to the lumen, has a longitudinal axis, has a second end disposed opposite the first end of the second end protector along the longitudinal axis, has a transverse axis having a diameter, wherein the second end protector is permeable along at least part of the longitudinal axis, and wherein the second end protector is rigid or expansile to keep tissue from collapsing or sagging into the lumen. In some embodiments, the body is permeable. In some embodiments, the body is impermeable. In some embodiments, the body is covered with an impermeable film. In some embodiments, the second end of the second end protector is closed or capped. In some embodiments, the closed or capped second end of said second end protector is permeable. In some embodiments, the closed or capped second end protector is impermeable. In some embodiments, the diameter of the transverse axis of the body is the same as the diameter of at least part of the transverse axis of the second end protector. In some embodiments, the diameter of the transverse axis of the body is greater than the diameter of at least part of the transverse axis of the second end protector. In some embodiments, the diameter of the transverse axis of the device body is less than the diameter of at least part of the transverse axis of the second end protector. In some embodiments, the diameter of the transverse axis of said body is expandable from a first diameter to a second diameter. In some embodiments, the device further comprises a first space extension having a first end joined to the first end of the body and fluidly connected to the lumen, a second end, a longitudinal axis, and a transverse axis, wherein the first space extension is permeable along at least part of the longitudinal axis. In some embodiments, the first space extension is closed at the second end. In some embodiments, the body is made of a mechanically-expandable material. In some embodiments, the body is made of a self-expanding material. In some embodiments, the self-expanding material is nitinol. In some embodiments, the first space extension is made of a self-expanding material. In some embodiments, the device is coated with an antibiotic. In some embodiments, the device is radio-opaque. In some embodiments, the device is made of a magnetic resonance imaging (MRI)-compatible metal. In some embodiments, the device is coated with an antibiotic.

In a second group of embodiments, the invention provides methods for relieving pressure on a patient's organ due to trapped fluid. The methods comprise implanting in the organ a device to divert trapped fluid from the organ to an adjacent body cavity, the device comprising a body and a second end protector, wherein (a) the body is tubular and has a transverse axis having a diameter, is permeable or impermeable, has a first end and a second end and has a lumen fluidly connecting the first and second ends, and, (b) the second end protector extends from said second end of said body, has a first end joined to the second end of said first section and fluidly connected to the lumen, has a longitudinal axis, has a second end disposed opposite said first end of the second end protector along the longitudinal axis, has a transverse axis having a diameter, wherein the second end protector is permeable along at least part of the longitudinal axis and wherein the second end protector is rigid or expansile to keep tissue from collapsing or sagging into the lumen. In some embodiments, the body is permeable. In some embodiments, the body is impermeable. In some embodiments, the body is coated with an impermeable films. In some embodiments, the second end of the second section end protector is closed or capped. In some embodiments, the closed or capped end of said second end protector is permeable. In some embodiments, the closed or capped end of said second end protector is impermeable. In some embodiments, the diameter of the transverse axis of the body is expandable from a first diameter to a second diameter. In some embodiments, the second diameter of the transverse axis of the body is the same as the widest diameter of the transverse axis of the second end protector. In some embodiments, the second diameter of the transverse axis of the body is less than the widest diameter of the transverse axis of the second end protector. In some embodiments, the second diameter of the transverse axis of the body is less than the widest diameter of the transverse axis of the second end protector. In some embodiments, the organ is the patient's brain. In some embodiments, the device comprises a first space extension having a first end joined to the first end of the body and fluidly connected to the lumen, a second end, a longitudinal axis having terminating in said second end and a transverse axis, wherein the first space extension is permeable along at least a part of the longitudinal axis. In some embodiments, the first space extension is closed at the second end. In some embodiments, the body is made of a mechanically-expandable material. In some embodiments, the body is made of a self-expanding material. In some embodiments, the first space extension is made of a self-expanding material. In some embodiments, the device is radio-opaque. In some embodiments, the device is made of a magnetic resonance imaging (MRI)-compatible metal. In some embodiments, the device is coated with an antibiotic.

In yet another group of embodiments, the invention provides implantable devices for transferring fluid from a patient's organ. The devices comprise a tubular body having a longitudinal axis and a lumen, which body has (i) a first section having a first end and a second end at opposite ends of the longitudinal axis and a transverse axis expandable from a first diameter to a second, larger diameter, (ii) a second section extending from the first section along the longitudinal axis and having a first end and a second end having respective diameters, wherein the diameter of the second end is smaller than the diameter of the first end, and (iii) a lumen fluidly connecting the first end of the first section to the second end of the second section. In some embodiments, the body is permeable. In some embodiments, the body is impermeable. In some embodiments, the body is coated or covered with an impermeable film. In some embodiments, the first section is made of a self-expanding material. In some embodiments, the first section is made of a mechanically expandable material. In some embodiments, the device is radio-opaque. In some embodiments, the device is made of a magnetic resonance imaging (MRI)-compatible metal. In some embodiments, the first section has openings positioned to permit fluid to enter into the lumen from at least two separate spaces within the organ. In some embodiments, the second section is of a length to terminate at the surface of the patient's body. In some embodiments, the second end of said second section has a diameter suitable for insertion into medical tubing. In some embodiments, the organ is the patient's brain.

In still additional embodiments, the invention provides methods of transferring fluids from a patient's organ to a desired destination by using the devices of any of the embodiments described in the preceding paragraph.

In another group of embodiments, the invention provides systems for transferring fluid from a patient's brain, the system comprising: (a) a device having a tubular body with a longitudinal axis and a lumen, which body has (i) a first section having a first end and a second end at opposite ends of the longitudinal axis and a transverse axis expandable from a first diameter to a second, larger diameter, (ii) a second section extending from the first section along the longitudinal axis and having a first end and a second end having respective diameters, wherein the diameter of the second end is smaller than the diameter of said first end, and (iii) a lumen fluidly connecting the first end of the first section to the second end of the second section, and (b) a skull port piece. In some embodiments, the skull port piece is circular and has a central lumen. In some embodiments, skull port piece has an internal lip surrounding the lumen. In some embodiments, the skull port piece has an external helical ridge. In some embodiments, skull port piece lumen has an helical ridge. In some embodiments, the second end of the second section has extensions that can be pressed against the internal lip of the skull port piece. In some embodiments, the system further comprises a reservoir. In some embodiments, the reservoir is of silicon. In some embodiments, the reservoir has a port. In some embodiments, the skull port piece has an internal lip surrounding the lumen. In some embodiments, the reservoir has a rim sized to the lip of the skull port piece. In some embodiments, the system further comprises a locking ring that compresses the reservoir rim against the lip of the skull port piece. In some embodiments, the second end of the second section has prongs or other extensions, which prongs are held in place against the lip of the skull port piece by the reservoir rim and locking ring. In some embodiments, the body is made of a self-expanding material. In some embodiments, the device is radio-opaque. In some embodiments, the device is made of a magnetic resonance imaging (MRI)-compatible metal. In some embodiments, the system further comprises a valve.

In still additional embodiments, the invention provides methods of transferring fluid from a patient's brain to a desired destination by using the systems of any of the embodiments described in the preceding paragraph.

BRIEF DESCRIPTION OF THE DRAWINGS

In FIG. 1, the first end 12 of the device terminates in a brain ventricle 13 to relieve pressure from cerebrospinal fluid trapped in the ventricle. In the particular embodiment shown, first end 12 does not extend into the ventricle, 13. The body 14 of the device extends from the ventricle 13, which in this example is the first space, through the brain parenchyma 15 to the second end protector 16, which is in the subarachnoid space 17, between the arachnoid membrane (part of the meninges, 18) and the brain parenchyma 15. In the particular embodiment of the device shown in FIG. 1, second end protector 16 expands outward as it extends into the subarachnoid space 17 and then narrows again to form a surface 19 providing support to the meninges 18. A lumen 22 extends from the first end 12 through the device body 14 to the second end protector 16, providing fluid communication between the ventricle 13 and the subarachnoid space 17, thereby allowing excess cerebrospinal fluid in ventricle 13 to exit into subarachnoid space 17. The support provided by surface 19 of the second end protector 16 to the arachnoid membrane 18 prevents the meninges 18 from sagging into the subarachnoid space 17 and obstructing the flow of fluid from the device, which could occur if, for example, fluid accumulates in the subdural space in the area around where the device was implanted.

In FIG. 5, the first end 42 of the device terminates in a brain ventricle 43 to relieve pressure from cerebrospinal fluid trapped in the ventricle. The body 44 of the device extends from the ventricle 43 through the brain parenchyma 45, through the subarachnoid space 46, through the arachnoid membrane 47 and the subdural cavity 48 to the skull 41 (the dura mater, a membrane attached to the interior of the skull 41, is not shown). The second end 50 of the device tapers to fit into the lumen 51 of the skull port piece 52, and fluidly connect to reservoir 53. Reservoir 53 has a port 54 to which medical tubing 55 is attached. Lumen 56 fluidly connects first end 42 to second end 50 and allows fluid in ventricle 43 to be diverted into reservoir 53 and to tubing 55. A locking ring (visible in section just above the reservoir lip) may be used to secure the reservoir 53 to the skull port piece 52.

DETAILED DESCRIPTION

Figure 1:
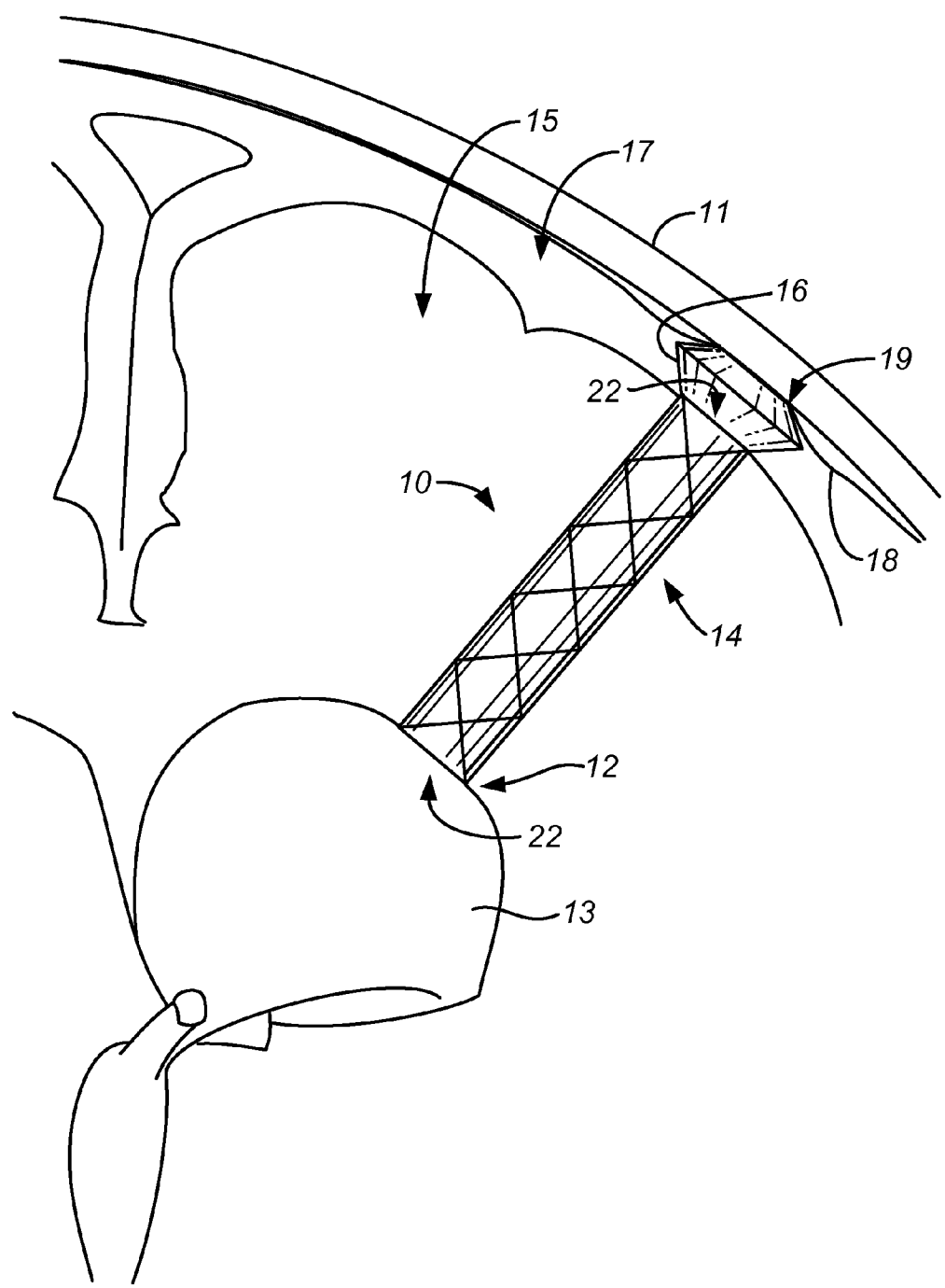
FIG. 1 depicts a device 10 within this group of embodiments positioned within the skull 11 of a patient diagnosed with hydrocephalus.

As noted in the Background, the abnormal accumulation of fluids within organs, such as the liver, spleen, kidney, pancreas, or brain, can create pressure on those organs resulting in damage and pathology. Surprisingly, the present disclosure provides new devices, systems and methods to relieve overpressure on organs from fluid accumulating in spaces within the organ, thereby ameliorating symptoms due to that overpressure. Devices of the first group of embodiments disclosed below are particularly useful in enabling the practitioner to equalize pressure between two adjacent body spaces. For example, a device of this group of embodiments can be used to equalize pressure between a brain ventricle and the subarachnoid space, reducing the risk of damage to the brain from overpressure originating in either of those spaces. Devices of this group have specialized endings to prevent collapsing or sagging tissue from obstructing their lumens. Devices of the second group of embodiments disclosed below enable the practitioner to divert fluid from one area of a patient's body to another or to a location outside the patient, such as a collection receptacle. Devices of this group of embodiments have specialized endings that facilitate securing tubing to the devices to conduct the fluid away from the area of overpressure. Further surprisingly, some devices of the second group of embodiments can be used in the treatment of complex, or loculated, hydrocephalus, Dandy-Walker syndrome, and other conditions which are currently difficult to treat with conventional devices and often require multiple shunt systems and multiple revisions.

A. Devices Permitting Diversion of Fluid within the Patient's Body to its Normal Physiological Destination 1. Introduction In a first group of embodiments, the invention relates to devices that permit fluid creating overpressure in a space or cavity within an organ to exit the organ while reducing damage to the organ to the extent possible. This is achieved by using the device to create a new extraluminal pathway for fluid to flow through the organ to its normal physiological destination within the patient's body, such as another ventricle, cistern, or the subarachnoid space. The devices can be used in any organ in which an undesirable fluid overpressure has arisen but in preferred embodiments, the organ is the brain, kidney or liver. For the reader's convenience, the exemplar embodiments of the devices described in the sections below focus on devices sized for use in the brain, which will typically be implanted by neurosurgeons. Devices for use in a kidney or the liver would have the same design as described in this Section, but larger dimensions, as noted in more detail below. The persons of skill who will be performing implantation of a device in a patient's kidney or liver will typically be experienced surgeons with specialized training in urology or hepatology, respectively. Selection of a device of a width and length appropriate for placement in a particular organ of a particular patient is well within the expertise of these highly trained and experienced persons of skill in the art.

This section first provides an overview of the features of the devices of this group of embodiments. Once the overview of the devices has been provided, the different sections of the devices of this group of embodiments are discussed in some detail. While sections of the devices are discussed separately to better explain some of their advantages and details, persons of skill will understand that the devices themselves are not necessarily made of different pieces joined together; the devices themselves may be made in one piece or of a plurality of components joined together.

For ease of reference, the space in which the fluid is causing an overpressure will sometimes be referred to herein as the "first space" and the location to which the fluid is being diverted will be referred to herein as the "second space." In the case of obstructive hydrocephalus due to overpressure of cerebrospinal fluid (CSF) in a brain ventricle, for example, the brain ventricle would be the "first space." If the CSF is then diverted to the subarachnoid space by a device of these embodiments of the invention, the subarachnoid space would be the "second space."

While intracranial pressure in the brain is most commonly caused by overpressure in a ventricle, persons of skill will recognize that overpressure can also occur in the subarachnoid space and that it is undesirable that pressure be unequal between the ventricles and the subarachnoid space. Persons of skill will recognize that the devices of this group of embodiments will equalize pressure between any two body compartments connected by one of the devices regardless of which initially has a higher pressure relative to the other. Thus, while the devices have been described below in terms of permitting fluid to flow from the first end to the second end, in practice the devices will also allow fluid to flow from the second end to the first end if the pressure is higher in the second than in the first. Thus, the devices can be used to equalize the pressure of any two body compartments connected by the devices regardless of which compartment initially has a higher pressure. It is anticipated that the devices will typically be inserted from the exterior of the organ (as opposed to being introduced by a guide wire fed up through a vein from the interior of the organ), and will therefore will always be inserted in the same orientation, with the second end protector being closer to the surface of the body than the first end, regardless of the direction fluid will flow between compartments. For convenience of reference, therefore, the discussion below will assume that the fluid flow is from the first space to the second space, even though in some embodiments the fluid flow may be the opposite.

2. Overview of Devices of this Group of Embodiments

The devices of this group of embodiments have a body, which is typically tubular in shape. The body has a length that is selected for the particular patient and the organ in which it is to be placed, such that the body will extend through the parenchyma of the patient's organ from the first space to the second space. For example, if the device is intended to relieve pressure in the brain of a patient with obstructive hydrocephalus, the body will be selected to have a length sufficient to extend through the brain parenchyma from the brain ventricle in which the overpressure is present to the subarachnoid space. The body further has two ends, a first end and a second end, which are disposed opposite each other along the length of the body, and a lumen fluidly connecting the two ends (and which in use fluidly connects the first space to the second space). For convenience of reference, the term "first end" will be used to refer to the end of the body intended to contact the first space (in the example above, the ventricle) and the term "second end" will be used to refer the end of the body intended to contact the second space (in the example above, the subarachnoid space). In some embodiments, the body length is selected so that in use the first end will be positioned at the point at which the device penetrates through the parenchyma into the first space, thereby placing the lumen of the body in direct contact with fluid in the first space, while in other embodiments, it may be selected so that the body extends into the first space. To facilitate describing the portion of the device body intended to extend into the first space in these embodiments and differentiating it from the portion of the body intended to traverse organ parenchyma, the portion of the body extending into the first space will sometimes be referred to herein as the "first space portion" of the body, while portions of the body intended to remain surrounded by the parenchyma of the organ when the device is in place will be referred to as the "organ portion" of the body.

As noted, the body of the devices of this group of embodiments further have a second end intended to be positioned in use at or within the second space. Extending from or attached to the second end of these devices is a "second end protector" which extends into the second space and which serves several purposes. First, the second end protector reduces the possibility that debris or tissue in the second space (including but not limited to meninges and brain parenchyma) will block the exit of fluid from the second end of the body. Second, in some embodiments, the second end protector provides a support that prevents the arachnoid membrane, dura, or other tissue (such as scar tissue) adjacent to the second space from sagging or collapsing onto the second end lumen and thereby obstructing flow of fluid from the device body into the second space. As one function of the second end protector is to prevent obstruction of the lumen, it is preferable that the second end protector have sufficient rigidity or expansile properties both radially and longitudinally to keep a space open around the lumen of the device.

As will be discussed further below, the first end, first space portion and the organ portion of the body are designed to be introduced into position in a low profile, small diameter configuration and deployed in situ to a larger functional diameter. The second end protector does not necessarily need to be designed to be introduced in a low profile, small diameter configuration. Use of a low profile small diameter configuration for the second end protector, however, allows use of a smaller opening into the patient's body into which to introduce the device, and it can be used in some embodiments.

In some embodiments, the device can be recollapsed and removed if necessary, for example, because infection has occurred or the patient has a reaction to the material of the device. Collapsing the second end protector can typically be physically accomplished in the second space. Collapsing the body of the device can typically be achieved by advancing a sheath over the body. As the lumen of the sheath is the size of the collapsed device, sliding the sheath over the body compresses the body back to its original size for removal.

3. First End and First Space Region

In most embodiments of devices of this group of embodiments, the length of the body is selected so that either (1) the first end is positioned in use at the point the body emerges from the organ parenchyma into the first space, placing the lumen of the body in contact with fluid in the first space, or (2) the body has a first space portion extending into the first space, placing the lumen of the body in contact with fluid within the first space.

Current methods of relieving pressure in brain ventricles include inserting tubing into the ventricle. Because the insertion of a tube into the brain cuts a circle of white matter equal to the diameter of the tube, practitioners have used tubes with narrow diameters, typically with a lumen of less than 2 mm. These tubes frequently become clogged and consequently fail to relieve pressure in the ventricle. Devices of the group of embodiments under discussion in this section solve this problem in several ways. First, since the first end, any first space portion, and the organ portion are introduced into the organ in a collapsed or compact form and then expanded (preferably slowly) to a larger diameter, the devices of this group of embodiments can have a lumen larger than the tubes which have typically been used to date, while reducing damage to the organ parenchyma because the cells (for example, the white matter tracts in the case of the brain) are splayed apart instead of cut. The lumen of the devices used in the devices under discussion are typically about 2-25 mm, preferably about 3-20 mm, more preferably about 3-15 mm, still more preferably about 3-10 mm, even more preferably about 3-9 mm, yet more preferably about 3-8 mm, in some embodiments preferably about 4-7 mm, in others preferably about 4-6 mm, and most preferably about 5 mm, with "about" meaning +/−0.5 mm. The larger lumen afforded by many of the devices of this group of embodiments significantly reduces the possibility the lumen will become obstructed in use. Second, the adaptations to the first end or first space portion discussed below protect the lumen from blockage and provide a surface area larger than the lumen itself through which fluid can reach the lumen, thus reducing the possibility of blockage even of devices with lumens smaller than or comparable to the tubes that have typically been used to date. Third, the devices of this group of embodiments can be if needed easily reaccessed and unclogged without removal or replacement. Thus, the devices of this group of embodiments are much less likely to become clogged than are the tubes currently used and if necessary can be unclogged in situ, reducing the risk of bleeding that could accompany removal of an implanted device or of infection from insertion of a new one.

The first space portion can be made of permeable material, or of impermeable material but with one or more openings permitting fluid in the first space to enter into the body of the device. For example, the first space portion can be a solid sheet rolled or otherwise formed into a tube or can be made of a mesh which has an impermeable coating. The one or more openings in the first space portion can be at its terminus, can be along its length, or both. Where the first space portion is permeable, as in embodiments in which it is a mesh or weave that is loose enough to have openings along its length, fluid will enter through the openings and, if the terminus also has one or more openings, through the one or more openings in the terminus as well.

In some situations, including ependymal lining, ventricular wall collapse (slit ventricles), or scarring, it is possible that debris or tissue could come into contact with the lumen of the first end or of the first space portion. The first end or first space portion is optionally therefore adapted to prevent debris or tissue from obstructing the flow of fluid into the first end or first space portion. Persons of skill will recognize that a number of ways exist in the art for adapting the first end or first space portion to prevent tissue or debris from restricting fluid entering the device.

In some of these embodiments, the first space portion is formed so that it continues the lumen of the device body for some distance into the first space and then is closed at its terminus by bending inward the material forming the first space portion. In these embodiments, the sides of the first space portion will either be permeable or will have one or more openings permitting fluid in the first space to enter the lumen of the body and flow to the second end. For example, the first space portion may have a plurality of small openings permitting the flow of fluid, or may be a mesh, netting, or web of woven, welded, or soldered fibers. In many embodiments, the first space portion will be metal, but it can be of other materials, such as a biocompatible polymer, so long as the material has sufficient rigidity or expansile properties not to collapse over the lumen while in use (as used herein, "expansile properties" denotes a property by which material used in a recited element of the device exerts an outward force in all directions, thereby maintaining the intended dimensions of the element against any pressure that is normally present at the location in which the device is to be implanted). A number of suitable biocompatible polymers are known in the art, such as those set forth in U.S. Pat. No. 8,043,363, column 6.

In other embodiments, the first space portion maintains the diameter of the lumen as it enters into the first space and then narrows to a point at which any opening remaining will be too small (for example, 1-5 mm) for tissue or debris to enter. As in the embodiments discussed above, the first space portion is typically either made from a permeable material or made from impermeable material, but with a plurality of holes or other openings to permit fluid to enter the lumen of the first space portion. Typically, the holes or other openings are small enough to keep debris or tissue from entering. The first space portion of these embodiments can be made of the same materials as discussed in the previous paragraph.

In yet other embodiments, the first end or first space portion is adapted by having a cap which closes off the lumen or hollow of the first end or first space portion, thereby preventing entry of tissue or debris. The cap can be permeable or impermeable. For devices in which the first end is positioned at the juncture of the organ parenchyma and the first space (and which therefore do not have a first space portion of the body), permeable caps are preferable to permit fluid to enter the lumen. The cap does not need to lie flat against the first end and may form a tent over the end to provide a larger surface area for fluid to flow into the lumen of the first end.

The cap can be integral to the first end or first space portion, or can be affixed to it. For example, the cap can have one or more prongs and can be affixed to the first end or first space portion by positioning the cap over the terminus of the first end or first space portion and then bending the one or more prongs onto or through receiving surfaces on the first end or first space portion. Alternatively, the cap can be soldered or spot welded to the first end or first space portion. In yet another example, the cap can be bonded to the first end or first space portion by an adhesive. In still another, the first end or first space portion can be formed to have ridges onto which the cap can be screwed. Optionally, some or all of the first end or first space portion is radioopaque to facilitate visualizing its location while in the patient.

As noted earlier in this section, for most devices of this group of embodiments, it is desirable to reduce damage to the organ by not having the first space portion be long enough to extend across the first space into the tissue or parenchyma on the opposite side from where the first end enters the first space. In a subset of devices designed to fenestrate cysts or septum pellucidum, the practitioner may choose to have the device do so. As the end of the first space portion may in these embodiments be embedded in the parenchyma, fluid in the first space will necessarily have to enter the body of the device through openings in the circumference of the first space portion as it traverses the first space. Further, the length of the first space region is preferably selected to minimize damage to the opposite side organ parenchyma by extending only a short distance into the opposite side parenchyma.

4. The Body

The preceding section discussed the first end and first space portion of the body of devices of the group of embodiments under discussion. This section focuses primarily on the organ portion of the body, that is, the portion expected in use to be situated within the parenchyma of the organ the device traverses.

The organ portion of the body can be permeable or impermeable. It is not expected that the pressure of fluid transiting from the first space to the second space will be sufficient to cause substantial leakage from the organ portion into the organ parenchyma. Nonetheless, to reduce the possibility of edema, in preferred embodiments, the organ portion of the body is preferably not permeable. Methods and materials for making stents that are coated with an impermeable film or coating or otherwise made impermeable are known in the art, as exemplified by U.S. Pat. No. 7,914,568, which is incorporated herein by reference. Similarly, methods are known of making stents from thin rolled sheets of metal, as discussed in U.S. Pat. No. 7,455,753. It is contemplated that these and other methods and materials known in the art can be used or readily adapted in making impermeable embodiments of the organ portion of the device body.

The body may optionally contain a valve system to permit drainage of fluid that has a pressure higher than that determined by the valve selected. Such valve systems are preferably expandable and resistant to clogging. Suitable valve systems include adapted bicuspid or tricuspid valves conventionally used in endovascular heart valve repair. The valves are preferably tubular and expandable and reduced in size to fit within the device body. Valves that open at several pressures are currently available for use in heart valve repair, and it is expected that the highly skilled practitioners in this art can select a valve of a size and opening pressure suitable for use in the devices herein.

5. The Second End and Second End Protector

The devices of this group of embodiments further have a second end positioned at the terminus of the length of the body opposite the first end. The second end terminates at the second space and has a second end protector that extends into the second space. The second end is hollow or has a lumen and the lumen or hollow is fluidly connected to the lumen of the body.

As discussed above, the second end protector "tents" the lumen of the second end, thereby protecting it from being obstructed by debris or tissue in the second space. In this regard, the adaptations discussed above with regard to the first space portion can generally be used to prevent tissue or debris from obstructing the second end. Unlike the first space portion, however, the second end protector does not necessarily have to pass through the parenchyma of the organ when the device is being put in place, and accordingly is not constrained by needing to be able to be expanded from a first diameter to a second, larger diameter. This permits a wider range of shapes than may be usable for the first space portion. The diameter of the second end protector can optionally be larger than that of the device body (although still small enough to fit within the second space and through the incision or burr hole used by the practitioner to place the device). Alternatively, the second end protector may also be expandable to allow for a smaller incision/burr hole. In some embodiments, an expansile property of this portion of the device is preferable to facilitate tenting. Persons of skill will appreciate that it is desirable that the second end protector does not interfere with the normal movement of fluid in the second space and may be of a mesh-like configuration with large openings that do not impede fluid movement.

In some embodiments, the second end protector also serves to provides support for adjacent structures, helping prevent obstruction of fluid flow from the second end by tissue sagging or collapsing into the second space. For example, where the second space is the subarachnoid space, a combination of the pulsatile nature of CSF flow, gravity and scarring due to the implantation of the device can cause the arachnoid membrane and dural membrane to spontaneously collapse down, potentially obstructing the lumen of the device at the second end. Similarly, scarring subsequent to implantation of the device could cause a narrowing of the subarachnoid space, which could in turn obstruct flow from the lumen at the second end. Furthermore, accidental transfer of fluid into the subdural space (rather than into the subarachnoid space) could produce undesirable consequences such as subdural hygroma formation. The second end protector, by providing support for the subarachnoid and dural membranes, prevents a sagging or scarred membrane from blocking fluid flow from the second end into the second space or diverting CSF into the subdural space. The second end protector may be designed to present a substantially flat surface adjacent to the interior of the adjacent structure, such as the arachnoid membrane, or with a shape that generally conforms to the interior surface of the structure underneath the skull. The second end protector further preferably has expansile properties or sufficient rigidity to provide support for the adjacent structure. For example, if the second space is the subarachnoid membrane, the second end protector should have sufficient rigidity to support the arachnoid membrane, preventing it from narrowing the subarachnoid space due to pressure on the membrane from fluid in the subdural cavity, gravity, or scarring.

Persons of skill will recognize that, as with the first space portion, a number of ways exist for adapting the second end protector to prevent obstruction of fluid exiting from the second end extension. In some embodiments, the second end protector is formed so that it continues the lumen of the device body into the second space and then is closed at its terminus distal to the body by bending the material forming the second end protector inward until any lumen remaining at the terminus of the second end protector will be too small for tissue or membrane to enter. (For the sake of clarity, it is noted that the second end protector is in contact with, and attached to, the body of the device.) In other embodiments, the second end protector continues the diameter of the lumen into the second space and then narrows to a point at which any opening remaining will be too small (for example, 1-5 mm) for tissue or membrane to enter into the second end extension and obstruct fluid flow. (Once again, it is noted that the tenting of the second end provided by the second end protector provides a large surface area around the second end through which fluid can flow.) In some preferred embodiments, the second end protector is tubular or cylindrical and has openings around its circumference. In some preferred embodiments, the second end protector is in a configuration, such as a sphere, diamond shape, that is larger than the diameter of the body of the device, thereby forming a "tent" protecting the lumen of the second end.

In yet other embodiments, the second end protector is adapted by having a cap which closes off the lumen or hollow of the second end protector, thereby preventing entry of debris or tissue. The cap can be permeable or impermeable. The cap can be integral to the second end extension or can be affixed to it. For example, the cap can have one or more prongs extending outward and can be affixed to the second end protector by positioning the cap over the terminus of the second end protector and then bending the one or more prongs onto or through receiving surfaces on the second end protector. Alternatively, the cap can be soldered or spot welded to the second end protector. In yet another example, the cap can be bonded to the second end protector by an adhesive. In still another, the second end protector can be formed to have ridges onto which the cap can be screwed. The cap is preferably affixed before the device is implanted into the organ.

In all these embodiments, as least a portion of the circumference of the second end protector as it extends from the body into the second space has openings permitting the flow of fluid from the body through the second end into the second space while preventing the entry of debris or tissue. For example, the portion of the second end protector proximal to the body of the device may have a plurality of small openings permitting the flow of fluid, or may be a mesh, netting, or web of woven, welded, or soldered fibers. The second end protector may be made of metal, but it can be of other materials, such as a biocompatible polymer, so long as the material has sufficient rigidity to extend into the second space without collapsing. A number of suitable biocompatible polymers are known in the art, such as those set forth in U.S. Pat. No. 8,043,363, column 6.

6. Description of Figures Showing an Exemplary Embodiment

Figure 2:
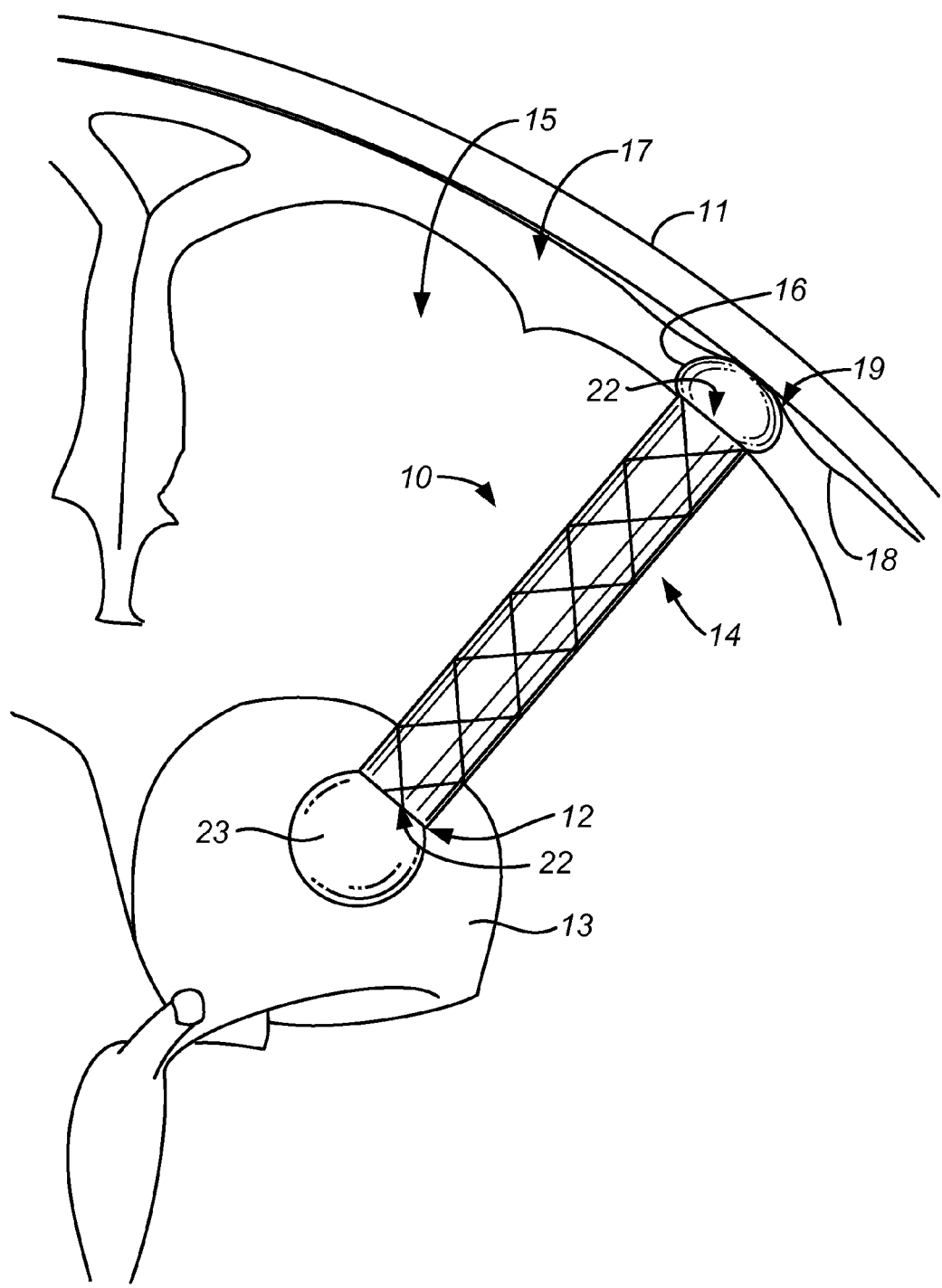
FIG. 2 shows another embodiment of a device to allow fluid trapped in a ventricle to be diverted to the subarachnoid space. The elements of FIG. 2 are as described for FIG. 1, except that second end protector 16 is shaped like an oval or ball and a first end protector 23 extends from first end 12

Some aspects of this group of embodiments may be better understood by reference to FIGS. 1 and 2. FIG. 1 depicts a device 10 within this group of embodiments positioned within the skull 11 of a patient diagnosed with hydrocephalus. In FIG. 1, the first end 12 of the device terminates in a brain ventricle 13 to relieve pressure from cerebrospinal fluid trapped in the ventricle. In the particular embodiment shown, first end 12 does not extend into the ventricle, 13. The body 14 of the device extends from the ventricle 13, which in this example is the first space, through the brain parenchyma 15 to the second end protector 16, which is in the subarachnoid space 17, between the arachnoid membrane (part of the meninges, 18) and the brain parenchyma 15. In the particular embodiment of the device shown in FIG. 1, second end protector 16 expands outward as it extends into the subarachnoid space 17 and then narrows again to form a surface 19 providing support to the meninges 18. A lumen 22 extends from the first end 12 through the device body 14 to the second end protector 16, providing fluid communication between the ventricle 13 and the subarachnoid space 17, thereby allowing excess cerebrospinal fluid in ventricle 13 to exit into subarachnoid space 17. The support provided by surface 19 of the second end protector 16 to the arachnoid membrane 18 prevents the meninges 18 from sagging into the subarachnoid space 17 and obstructing the flow of fluid from the device, which could occur if, for example, fluid accumulates in the subdural space in the area around where the device was implanted.

FIG. 2 shows another embodiment of this group of devices. The elements of this Figure are as described for FIG. 1, except that second end protector 16 is shaped more like an oval or ball and there is a first end protector 23 extending from first end 12.

7. Placement, Materials and Sizes

As persons of skill will appreciate, placement of the devices of this group of embodiments in an organ requires that the first end or the first space portion and the body be inserted through the parenchyma of the organ. To reduce damage to the parenchyma, the first end or first space portion and the body, and in some preferred embodiments, the entire device, is typically made from a material that can be inserted in a form having a first, small diameter, which can then expanded to a second, larger diameter. The first end or first space portion and the body typically have a tubular shape that is introduced in a compact or compressed form which once in position can be expanded to an expanded form. It is preferable that the expansion occur slowly to reduce damage to the tissue in which the body is situated.

Stents are endoluminal medical devices well known in the art for use in maintaining patency of blood vessels, ducts and other body passages. The devices of the group of embodiments under discussion in this section differ from stents not only because in use they are intended to be positioned in the parenchyma of an organ rather than in a lumen of a blood vessel or other body passage, but also because they have specializing endings not present in stents. The devices of the group of embodiments under discussion in this section, however, share with stents the need to be biocompatible and, for the first end or first space portion and for the body of the devices, to be capable of being introduced in a compact or compressed form and then expanded radially. Materials used for stents, and methods of introducing them, are therefore generally suitable for use with respect to devices of this group of embodiments. As with stents, the first end or first space portion and the body typically are designed to be self-expanding, mechanically expandable, or a hybrid of the two. Self-expanding devices may be made of shape memory metals such as nitinol, shape memory polymer materials, or constructed of non-shape memory metals but of a design which exhibits self-expansion characteristics. Devices made of metal are preferably made of a non-ferromagnetic, MRI-compatible metal, such as commercially pure titanium, Ti-6Al-4V or Ti-6Al-7Nb alloy, a cobalt-chromium alloy such as ASTM F75-12, F562-07 or F90-09, tantalum, or an stainless steel alloy that can be used in MRI environments, such as 316L, REX 734™, or 22-13-5. It is believed that nitinol and platinum are also suitable for use in MRI environments.

Devices in which the first end or first space portion and the body are mechanically expandable are typically delivered on a balloon and the balloon is used to the expand the first end or first end extension and body. Hybrid devices have both self-expanding properties and balloon expanding properties. Since, in use, any fluid flowing through the body of the device will be retained in the device by the surrounding parenchyma, the body can be permeable or impermeable, but in some preferred embodiments is impermeable. For example, the body can be made of a sheet of metal or biocompatible polymer, which sheet is fashioned into a tubular shape or covered with an impermeable film. If desired, the body can be coated with a film or other coating of a biocompatible polymer that contains an antibiotic. See, e.g., Gorman, S. and Jones, D., "Antimicrobial Biomaterials for Medical Devices," in Business Briefing: Medical Device Manufacturing & Technology, 2002, which can be found on the internet at touchbriefings(dot)com/pdf/753/mdev02_r_8.pdf. Films such as polycaprolactone incorporating the antibiotic rifampicin for use on medical devices have been reported. Biotech Equipment Update, p. 5 (Nov. 1, 2003).

For placement in the brain, a hole with a diameter sufficient for the second end protector is made in the skull and the device is introduced into the brain with the first space region, if any, and the body in a compressed or compact form positioned on an overwire balloon similar to those used in placing and expanding stents. The device is then expanded by inflating the balloon, after which the balloon and wire are removed. For placement in organs other than the brain, the device can be placed by catheterization or by open field surgery, depending on the organ and the practitioner's preference.

The second end protector does not need to be placed in a compressed or compact form, as it does not need to be inserted through the organ parenchyma, but it optionally can be expanded by the balloon as well. In embodiments in which a wire used for placement and balloon support runs through the second end protector, the second end protector will typically have a hole distal to the device body when the wire is removed. The hole is typically too small to allow the entry of debris or tissue that would block fluid flow but can, if desired, be closed by the practitioner. The second end protector can be manufactured with, for example, a short ring of extra material that can be pressed toward the center to close the hole. In some embodiments, the second end protector is affixed to the second end following placement of the body of the device in the brain or organ, in which case no hole will be present.

For embodiments intended for use in the brain, it is noted that the persons of skill in placing these embodiments are typically board certified neurosurgeons. It is further noted that the human anatomy of the skull is reproducible enough that anatomical landmarks can be used by these skilled practitioners to determine the location and length of the device needed to place the first end at or in the first space or to have it extend through the first space into the white matter when the device is inserted from a selected spot at an appropriate angle. In developed countries, however, it is anticipated that the patient will typically undergo preoperative imaging and that the distance to be spanned by the device will be measured on the images and the device selected accordingly. In addition, where available, intraoperative imaging can also be used during placement of the device to improve accuracy. Such imaging can include, but is not limited to, endoscopy, fluoroscopy, ultrasound, x-ray or navigation systems (such as optical, or radiofrequency systems).

Devices of this group of embodiments for use in organs other than the brain will typically be larger than those intended for use in the brain. For example, in some embodiments, devices for use in a kidney or the liver would have a width from 0.25 mm to about 5 cm and a length of 1 mm to about 40 cm, with "about" in this context meaning +/−0.5 cm. In other embodiments for these uses, the devices would have a width from 0.5 mm to about 5 cm and a length of 1 mm to about 20 cm, with "about" in this context meaning +/−0.5 cm. In still other embodiments for these uses, the devices would have a width from 1 mm to about 5 cm and a length of 2 mm to about 15 cm, with "about" in this context meaning +/−0.5 cm. In yet other embodiments for these uses, the devices would have a width from 0.5 mm to about 5 cm and a length of about 2 mm to about 10 cm, with "about" in this context meaning +/−0.5 cm. As discussed in connection with placement of devices in the brain, placement of devices in other organs will usually be guided by preoperative and intraoperative imaging, using techniques such as those described in the preceding paragraph.

B. Systems and Devices Permitting Diversion of Fluid to a Distant Body Cavity or External Receptacle

1. Introduction

In a second group of embodiments, the invention relates to systems and devices that relieve overpressure in an organ due to fluid in a space or cavity within the organ (in some embodiments within this group, the devices comprise several interacting components which are assembled at the time of implantation in the patient and thereafter relieve overpressure in the patient's organ. As used herein, the term "system" refers to these embodiments of interacting components and in particular the embodiments comprising a skull port piece, as discussed further below.) As in the group of embodiments described in Section A, above, this is achieved by using the systems and devices of these embodiments to create a new extraluminal pathway for fluid to flow from the organ. Unlike the first group of embodiments, however, this group of embodiments permits diverting the fluid to a location other than its normal physiological destination or adjacent body cavity. For example, the devices of this group of embodiments can be used to drain fluid from a cyst on a solid organ, such as the liver to the bile duct or to drain fluid from a cyst on an ovary to the pelvis or peritoneum. Devices of this group of embodiments have specialized ends permitting the devices to be attached to tubing or other conventional medical equipment. As described further below, in some embodiments, devices of this group of embodiments can be used to shunt fluid from two spaces at the same time to treat conditions in which this may be necessary.

The devices of this group of embodiments can be categorized as one of two types. The first type, which for convenience will be called category 1, has two subcategories, A and B. The devices of category 1A have a first end open at or in a cavity from which fluid is to be transferred, a second end designed to permit attachment of tubing or other medical equipment, and a lumen fluidly connecting the first and the second ends. "Designed to permit attachment of tubing" means that the second end of the device is sufficiently rigid that tubing can be slid over it (or it can be slid into tubing) without collapsing the lumen from the pressure of the tubing and, in preferred embodiments, that the second end has a protuberance, such as one or more bumps, ridges, lips or rims, helping hold the tubing to the second end. The protuberance also provides a point beyond which the practitioner can tie a suture to compress the tubing and prevent it from slipping over the protuberance. The second end can be attached to tubing which is tunneled subcutaneously to carry fluid to a desired location, such as the peritoneum, bladder or bile duct, or to an opening from which fluid can be deposited into an external receptacle, such as a colostomy bag. Alternatively, the second end can extend to or just beyond the surface of the patient's body, where it can be attached to conventional medical equipment, such as tubing.

The devices of category 1B have the same first end, but are designed for use in the patient's brain and the second end is sized to fit within the hole in the patient's skull used to implant the device (which hole for convenience can be referred to as the "burr hole"). In category 1B, the second end is of a length such that the second end is either accessible within the hole, is flush with the surface of the hole, or extends slightly from the hole to facilitate transfer of fluid to the receptacle or tubing.

In the second category, which for convenience may be referred to as category 2, the systems and devices are intended for placement in the patient's brain, as are those of category 1B, but the second end of the device fits into a piece (the "skull port piece") which is fitted to the burr hole (by, for example, being screwed into or glued to the burr hole) and which provides a location either for direct attachment of a receptacle or tubing or for a reservoir that connects to the second end directly or indirectly through the skull port piece, and which preferably has a port to which conventional equipment, such as tubing or a receptacle, can be attached. Use of a skull port piece reduces the chance of movement of the body of the device when tubing is changed or adjusted, and thereby reduces the risk of damage to the patient's brain from such movement. In preferred embodiments, the second end is secured to the skull port piece to lock the device and skull port piece together. Further, these devices may have a first end extender to cause the body of the device to lengthen as the patient's skull thickens over time. As these devices may be placed when the patient is a child but may need to divert fluid from the patient's ventricle as the patient matures into a teen and then a young adult, locking the device body to the skull port piece with a first end extender helps reduce the need to replace the device as the patient's skull grows.

For ease of reference, the space in which the fluid is causing an overpressure will sometimes be referred to herein as the "first space." In the case of obstructive hydrocephalus, for example, in which cerebrospinal fluid (CSF) causes the overpressure, the brain ventricle is the "first space" and the organ is the patient's brain. In an exemplar use of the devices of categories 1B and 2, the CSF is diverted from the brain ventricle through the device to a port in the patient's skull, where it can be connected to conventional tubing and then reintroduced into the patient via, for example, the abdomen. The devices of categories 1B and 2 are suitable for use in communicating hydrocephalus as well as in obstructive hydrocephalus.

2. Overview of Systems and Devices of this Group of Embodiments

The devices of both categories 1 and 2 have a body, typically tubular in shape, which has a length sized to extend from a body cavity with excess fluid pressure (the "first space") through the organ parenchyma to a position external to the body or, in the case of category 1B, at or above the skull or in category 2, within the skull port piece. The body of the device of each of these embodiments has two sections. The first section is designed to extend from the first space through the organ parenchyma and is typically designed to be introduced in a compact or compressed form and then expanded, preferably slowly, to reduce damage to the organ. The first section has a first end which has one or more openings to allow fluid in the first space and may be positioned at or within the first space or, in some embodiments, in the parenchyma opposite where the body of the device enters the first space.

The second section extends from the first section, but as it does not traverse organ parenchyma, does not need to be expandable. It has a first end connecting to the first section's second end and a second end from which fluid from the first space can be discharged. In categories 1B and 2, the second end typically tapers from the diameter of the expanded first section to a smaller diameter so that it can extend into a hole in the patient's skull, typically the burr hole made to introduce the device. The second end is disposed at the opposite side of the body from the first end along the length of the body. For category 1B, it is designed to permit attachment of tubing, as described for the second end of devices of category 1A. For category 1B, the second end is either (a) recessed within the skull but sufficiently close to the surface to be accessible for the attachment of tubing or the like to be attached to it, (b) flush the surface of the skull to permit attachment of tubing or the like, or (c) protrudes sufficiently beyond the surface of the skull to permit attachment of tubing or the like (but preferably not so far as to create a hazard or inconvenience for the patient). The body of the device (for each of the categories of this group) further has a lumen fluidly connecting the first end of the first section to the second end of the second section and which has openings at the first section's first end and the second section's second end allowing fluid to flow through the device body from one to the other. Optionally, a portion of the body, such as the first section's first end, is radiopaque to facilitate image guidance during placement and locating the device after placement. The body may also have a first space portion as described in Section A, above, and may be adapted to reduce the entry of debris or tissue into the lumen of the device.

As noted in the Introduction to Section B, the second end of the second section of the device body is adapted, depending on the category, either to connect directly to tubing or other conventional equipment for carrying fluids from a patient or to fit into a skull port piece which permits direct or indirect connection to tubing or other conventional equipment. In this regard, the second section will typically taper in diameter from its first end to its second end. The particular diameter of the second section's second end will be chosen depending on the practitioner's choice of equipment to which it is to be connected. Depending on the size chosen for the diameter of the second end, it can, for example, either fit into the lumen of conventional medical tubing or fit over the end of conventional medical tubing. It is also rigid enough so that the lumen is not constricted by compressive force from tubing placed over the end. In embodiments in which the second end is to be attached directly to medical equipment, such as tubing, it may have one or more bumps, ribs, ridges, lips, or other exterior protrusions to keep tubing placed over the second end from slipping off.

In systems of category 2, the second end is designed to be received by a skull port piece, which is typically screwed into, or glued to, the patient's skull. The second end is then available either for direct connection to conventional medical tubing while in position in the skull port piece or for indirect connection through having its fluid flow into the lumen of the skull port piece, or into a reservoir within the skull port piece, to which conventional medical tubing can be attached. The second end of these embodiments may further be adapted to lock the device to the skull port piece, as discussed further below.

3. The First End and First Space Region

The devices of this group of embodiments have a first end and, optionally, a first space portion, like those of the group of embodiments described in Section A, above. The description provided in Section A with regard to the first end and, optionally, first space portion of the body is equally applicable to the group of embodiments under discussion in this Section.

4. The Body

The devices of this group of embodiments have a body like that of the group of embodiments discussed in Section A, above. The description provided in Section A with regard to the body of the devices under discussion there is equally applicable to the group of embodiments under discussion in this Section.

As persons of skill will appreciate, in use, the body of devices of categories 1B and 2 of this group of embodiments will generally traverse, proceeding from first end to second end, the ventricle, brain parenchyma, then the subarachnoid space, the arachnoid membrane, the subdural cavity, and the dura mater. Thus, while a portion of the body of the device is in use surrounded by brain parenchyma, the portion distal to the first end traverses several spaces into which fluid would be lost if the material of the body was permeable. The portion of the body designed to be contained within the parenchyma when in use (for convenience of reference, this portion is sometimes referred to herein as the "parenchyma section" of the body) may be permeable or impermeable, but in some preferred embodiments is impermeable. The portion distal to the parenchyma section, that spans the subarachnoid space and the subdural cavity (for convenience of reference, this portion of the body may be referred to as the "spanning section") is preferably impermeable so that the fluid is not lost before it reaches the skull port or reservoir. For example, the spanning section can be made of a sheet of metal or an impermeable biocompatible polymer, or the section can be made of a permeable material which is coated or covered with an impermeable biocompatible film or coating, such as that discussed in Section A. It will further be appreciated that the spanning section does not need to have the same diameter as the parenchyma section along its entire length. The spanning section may maintain the diameter of the parenchyma section when it is expanded, may be larger (as the practitioner does not have to be concerned with it damaging brain parenchyma), or may narrow as it extends from the parenchyma section to the skull port to facilitate mating with the lumen of the skull port. For clarity it is noted that the parenchyma section and the spanning section may be two sections joined together but in many embodiments will be one continuous unit and that the variations in diameter noted are typically on the order of plus or minus 5 millimeters, may be plus or minus 4 millimeters, in some embodiments may be plus or minus 3 millimeters, and in preferred embodiments are plus or minus 2 millimeters.

As noted in the Introduction to this Section, there are some conditions in which it may be desirable to shunt fluid from two spaces at the same time. This is particularly true of some disorders affecting the brain. For example, in Dandy-Walker syndrome, a cyst in the posterior fossa and abnormal development of the cerebellum causes increased pressure from within the cyst and in the lateral ventricles secondary to compression of the cerebral aqueduct. One of the current treatments for Dandy-Walker syndrome is double shunting of a lateral ventricle and the posterior fossa with a multi-component implantable device. Unlike the devices described in the preceding paragraph, in embodiments intended to divert fluid from two spaces in the brain, the device will traverse a second cavity before exiting the skull (the subarachnoid space is not considered a cavity and in any event the subarachnoid space is for the most part non-existent over the cyst in Dandy-Walker syndrome). Another example where it may be desirable to have fluid entering the device at multiple portions is hydrocephalus with loculations or benign external hydrocephalus. In embodiments in which it is desirable to shunt fluid from two spaces (whether within the brain or in one or more other organs) the section intended to span the second cavity is preferably permeable or has holes permitting fluid in the second cavity to enter the lumen and flow (along with fluid from the first space) to the point at which it can be discharged into conventional medical equipment.

5. The Second End

The devices of this group of embodiments further have a second end positioned opposite the first end. As noted in the Overview discussion, the second end of devices of this group of embodiments is adapted to facilitate attachment of tubing or other conventional medical equipment, thereby allowing fluid from the first space to be shunted through the tubing to a destination of the practitioner's choice. Typically, the second end is adapted by having it narrow in diameter relative to the diameter of the rest of the device body. Further, as noted, the second end may have one or more bumps, ribs, ridges, flanges, or lips to help secure tubing to the second end while in use. In some embodiments, the second end and the tubing may be designed to engage one another. For example, the second end may have threads to engage threads in the equipment to be attached to the second end, or a shaped protrusion at the tip designed to engage a slot of matching shape attached to the tubing. The practitioner can then, upon twisting the tubing on the second end, releasably secure it to the second end.

In some embodiments, the second end can also have extensions to facilitate locking the device to the skull port piece. These embodiments will be discussed in the next section.

6. Skull Port Piece

In embodiments of category 2, the second end of the device fits into a skull port piece. The skull port piece typically has a cylindrical body sized for the thickness of the skull to which it is to be affixed, and has a lumen permitting the entry of fluid from the second end of the device body, an internal surface facing on the lumen, an external side surface, a top surface, and a bottom surface that faces into the patient's skull. The external side surface of the skull port piece may have a helical ridge forming a thread allowing the skull port to be screwed into the skull to fix the skull port piece in position. In these embodiments, the top surface of the skull port piece may have one or more grooves or indentations that can engage the tip of a screwdriver or other tool to screw the skull port piece into the skull. These embodiments also allow the skull port piece to be removed easily later if desired. In other embodiments, the top surface of the skull port piece has a flange holding the skull port in position on the patient's skull. If it is desired to further secure the skull port to the patient's skull, a biocompatible adhesive can be used on the side of the flange facing the skull to cause the skull port to adhere to the skull. In some embodiments, the skull port piece does not have a flange, but is secured in place with a biocompatible adhesive placed, for example, on the exterior side surface of the skull port piece. Embodiments without external helical ridges are particularly suitable for use in infants, whose skulls may be too soft or too thin to permit screwing in a skull port piece.

In some embodiments, the second end of the device may butt up against the skull port piece tightly enough that fluid flowing through the second end from the first space will be retained in the lumen of the skull port piece (or in the reservoir discussed below).

In some preferred embodiments, however, the bottom surface of the skull port piece is shaped like a washer, with a flat surface extending around the interior of the skull port piece, with a central hole connected to the lumen and sized to mate to the second end of the device. Typically, the second end of the body enters through the hole a short distance into the lumen of the skull port piece, allowing fluid from the first space to flow through the lumen of the second end into the lumen of the skull port piece. Preferably, the second end fits tightly enough in or to the skull port piece lumen so that fluid entering the lumen of the skull port does not leak from the skull port piece or second end into any surrounding space. In preferred embodiments, the second end of the body and the interior surface of the skull port piece are designed to engage each other to secure the second end to the skull port piece. For example, the second end may have a helical ridge matching a groove on the interior surface of the skull port piece permitting the second end to be screwed on to the skull port at the same time the skull port piece is being screwed onto the patient's skull. In other embodiments, the second end can have tines, prongs, or other extensions which can be pressed onto the washer-like bottom of the skull port piece, or the interior surface of the skull port piece may have slits into which corresponding male extensions on the second end can fit. In preferred embodiments, the second end is designed to engage releasably with the skull port piece so that the device, the skull port piece, or both, can be removed for cleaning or replacement if necessary.

The systems and devices may further comprise a reservoir. The reservoir is typically of a biocompatible polymer, such as silicon, or other material with some resilience and compressibility. Preferably, the polymer also can self-close over a small puncture. The reservoir typically has a top surface, a flat bottom, sides and preferably a port, which is preferably positioned at the top or side of the reservoir. The bottom and sides of the reservoir preferably fit within the lumen of the skull port piece, while the portion of the reservoir with the port will preferably extend beyond the skull port piece to make it accessible for medical equipment such as tubing, to be attached. In embodiments in which the second end of the device enters the skull port piece through the skull port piece bottom, the bottom of the reservoir has a hole placed to align with the lumen of the second end of the device, which either allows fluid from the second end to enter the reservoir through the hole, or which admits the second end into the interior of the reservoir, allowing fluid to fill it internally. In some other embodiments, the reservoir bottom can have an extension that fits through the hole in the bottom of the skull port piece and which then mates with the lumen of the second end of the device at or just below the skull port piece.

The reservoir preferably also has a lip around its bottom. In embodiments in which the second end has tines, prongs or other extensions and is intended to be advanced through the hole in the bottom of the skull port piece, the extensions are pressed onto the internal surface of the bottom, thereby securing the device to the skull port piece.

The systems and devices may further comprise a locking ring or cap to secure the assembly of the second end and skull port piece, and, if present, the reservoir. The locking ring is generally a circular piece sized to fit within the skull port piece, with a central hole sized to fit over the reservoir. (The locking ring can be advanced over the reservoir port in some embodiments by first tilting the ring over the port and then straightening it to lower over the reservoir itself, or by bending the port, which will have some flexibility, to permit the ring to be lowered to the skull port piece bottom.) The locking ring is then pushed down over the reservoir and, if the reservoir has a lip, compresses the lip over the prongs or other extensions of the second end that have been pressed down on the interior surface of the skull port piece bottom, locking the components of the system together. The locking ring may have tines, prongs or other extensions to engage with slits or other receiving surfaces on the interior surface of the skull port piece, or a thread (a helical ridge) to engage the interior surface of the skull port piece to hold the locking ring in place. The ring may have, for example, one or more prongs that mate with a vertical channel down the interior surface of the skull port piece, which at the appropriate height above the bottom of the skull port piece turns horizontal, allowing the locking ring to be given a twist, thereby securing the ring (and the reservoir lip and prongs of the second end of the device) to the skull port piece. In embodiments in which a reservoir is not used, the second end of the body provides an access point that allows connection to medical equipment, such as conventional shunt valves and peritoneal tubing. In embodiments in which a reservoir is used, the port acts as the access point for attachment of such equipment. The skull port piece or the reservoir may also contain a valve. The valve typically contains an internal mechanism which allows release of fluid into the tubing only when the pressure of the fluid in the reservoir or skull port piece is above that of normal CSF.

7. Description of Figures Showing Exemplary Embodiments

Figure 3:
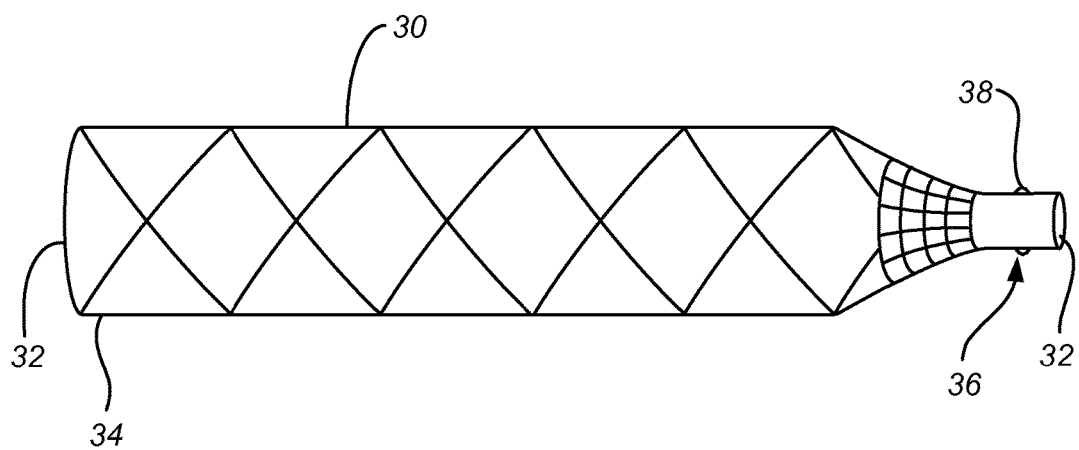
FIG. 3 depicts a device for diverting fluid trapped in an organ to medical tubing or other similar equipment. The device body 30 has a lumen 32 which connects the first end 34 to the second end 36. Specialized second end 36 is adapted to permit attachment of conventional medical tubing (not shown), typically by slipping the tubing over second end 36. Bumps 38 on second end 36 help hold tubing on second end 36 when the tubing is placed over the second end.
Figure 4:
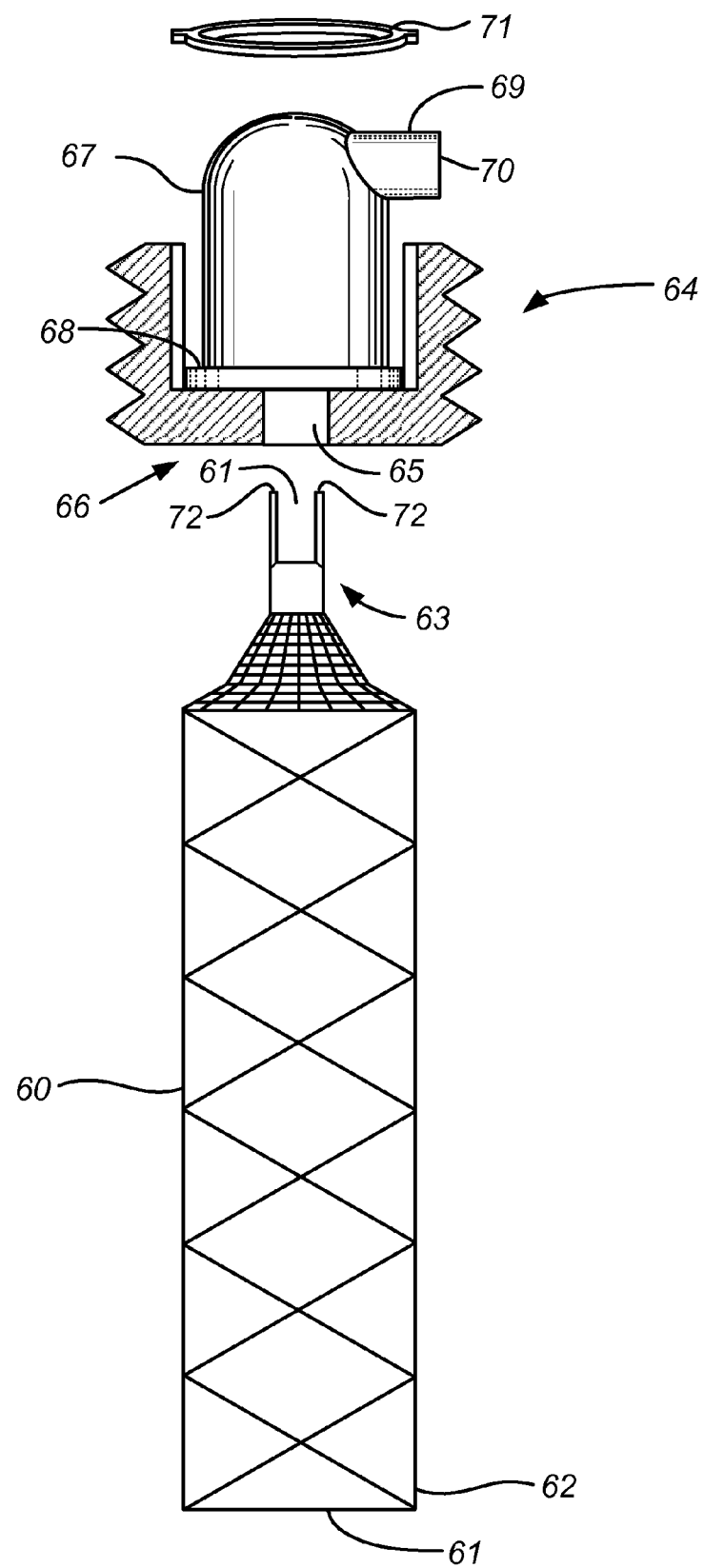
FIG. 4 depicts a system comprising a device 60 for diverting fluid trapped in a brain ventricle or other cavity and a skull port piece 64. The body of the device 60 has a lumen 61 connecting the first end 62 to the second end 63. Second end 63 fits into a hole 65 in the bottom of the skull port piece 64. Once advanced through the hole 65, prongs 72 can be pressed down against the internal surface of the bottom of skull port piece 64 to hold the device 60 to the skull port piece 64. The lumen 61 of second end 63 aligns with a hole in the bottom of reservoir 67, allowing fluid from first end 62 to enter the reservoir 67. Port 69 permits conventional medical tubing to be attached to the reservoir 67. End 70 of the port 69 can be cut before attaching the tubing to allow fluid in reservoir 67 to flow to a desired location. A locking ring 71 can be slid over the port 69 and reservoir 67. Extensions on locking ring 71 fit into threads (not shown) on the inside surface of skull port piece 64 to allow the ring to be screwed down onto reservoir lip 68 and prongs 72 (once they are pressed against the bottom of the skull port piece 64), locking second end 63, skull port piece 64 and reservoir 67 together.

Some aspects of this group of embodiments can perhaps be better understood by reference to FIGS. 2-4, which depict devices within this group of embodiments.

FIG. 3 depicts a device of category 1A of this group of embodiments. The device body 30 has a lumen 32 which connects the first end 34 to the second end 36. Second end 36 is adapted to permit attachment of conventional medical tubing (not shown), typically by slipping the tubing over second end 36. Bumps 38 on second end 36 help hold tubing on second end 36 when the tubing is placed over the second end.

FIG. 4 depicts a system of a device of category 2 of this group of embodiments with a skull port piece 64. The body 60 of the device has a lumen 61 connecting the first end 62 to the second end 63. Second end 63 fits into a hole 65 in the bottom of the skull port piece 64. Once advanced through the hole 65, prongs 72 can be pressed down against the internal surface of the bottom of skull port piece 64. The lumen 61 of second end 63 aligns with a hole in the bottom of reservoir 67, allowing fluid from first end 62 to fill the reservoir. Port 69 permits conventional medical tubing to be attached. End 70 of the port 69 can be cut before attaching the tubing to allow fluid in reservoir 67 to flow to a desired location. A locking ring 71 can be slid over the reservoir 67. Extensions on locking ring 71 fit into internal threads (not shown) on the inside surface of skull port piece 64 and allow the ring to be screwed down onto reservoir lip 68 and prongs 72, locking second end 63, skull port piece 64 and reservoir 67 together.

Figure 5:
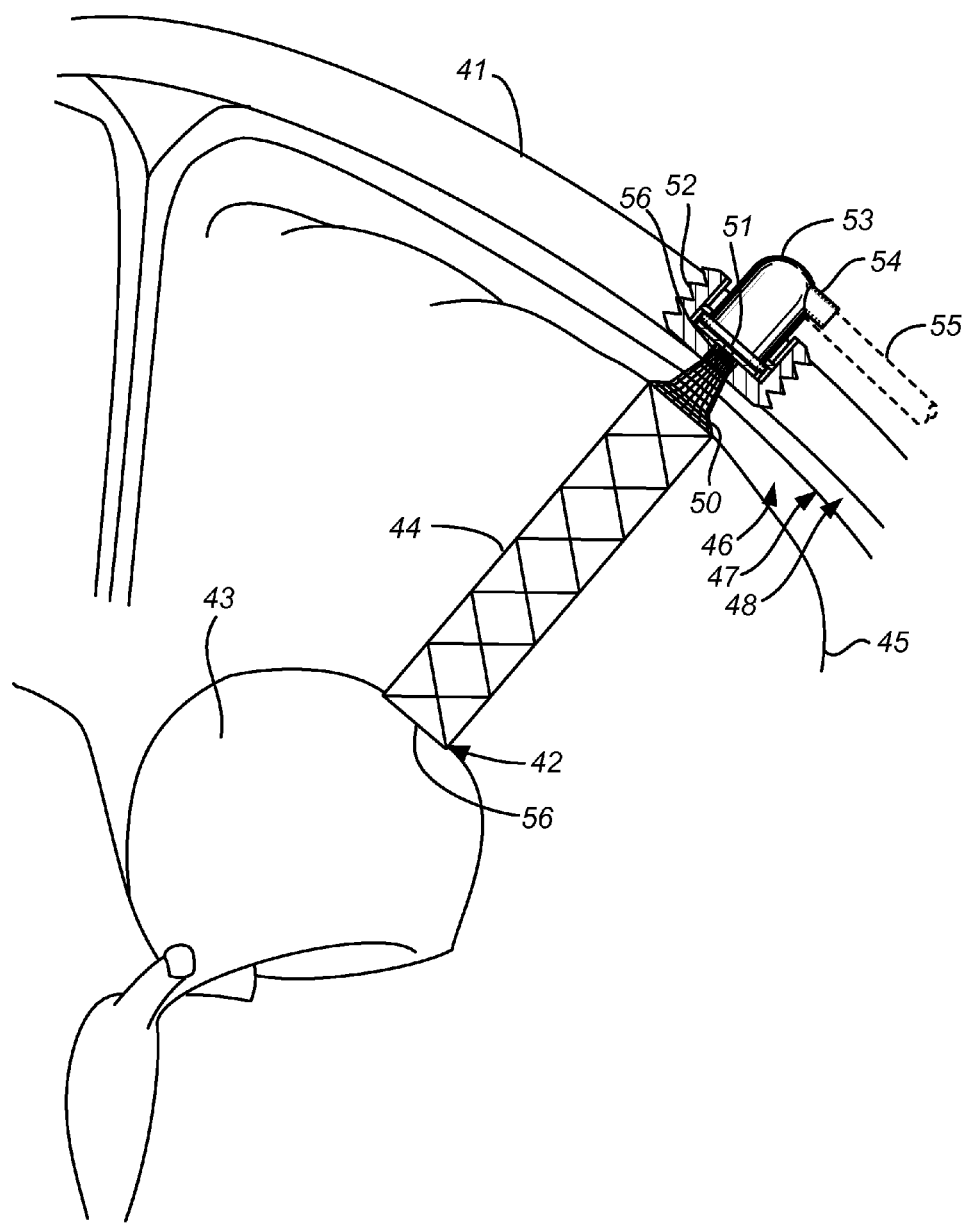
FIG. 5 depicts the system of FIG. 4 positioned within the skull 41 of a patient diagnosed with hydrocephalus.

FIG. 5 depicts the system of FIG. 4 positioned within the skull 41 of a patient diagnosed with hydrocephalus. In FIG. 5, the first end 42 of the device terminates in a brain ventricle 43 to relieve pressure from cerebrospinal fluid trapped in the ventricle. The body 44 of the device extends from the ventricle 43 through the brain parenchyma 45, through the subarachnoid space 46, through the arachnoid membrane 47 and the subdural cavity 48 to the skull 41 (the dura mater, a membrane attached to the interior of the skull 41, is not shown). The second end 50 of the device tapers to fit into the lumen 51 of the skull port piece 52, and fluidly connect to reservoir 53. Reservoir 53 has a port 54 to which medical tubing 55 is attached. Lumen 56 fluidly connects first end 42 to second end 50 and allows fluid in ventricle 43 to be diverted into reservoir 53 and to tubing 55. A locking ring (visible in section above the reservoir lip) may be used to secure the reservoir 53 to the bottom of skull port piece 52.

8. Materials and Placement

As discussed in connection with the devices of the embodiments in Section A, above, to reduce damage to the parenchyma as much as possible, the first end and the body are typically made from a material that can be inserted in a form having a small cross sectional area, which area can then be expanded. The first end and the body typically have a tubular shape that is introduced in a compact or compressed form which once in position can be expanded radially to an expanded form. It is preferable for the expansion to occur slowly as that can reduce damage to the parenchyma surrounding the device.

As with the devices disclosed in section A, above, the devices under discussion in this section differ from stents in part because in use the body of the device is positioned in the parenchyma of the brain rather than in a lumen of a blood vessel or other body passage (and of course are also different from stents in that they have a specialized end designed to connect with either the skull port piece or directly to tubing to permit the diversion of fluid from the first space to another location). Materials used in the art for stents, however, are generally useable for the body of the devices. As with stents, the body is designed to be self-expanding, mechanically expandable, or a hybrid of the two. Self-expanding devices may be made of shape memory metals such as nitinol, shape memory polymer materials, or constructed of non-shape memory metals but of a design which exhibits self-expansion characteristics. Devices in which the body is mechanically expandable are typically delivered on a balloon and the balloon is used to the expand the body. Hybrid devices have both self-expanding properties and balloon expanding properties. As noted in the discussion with regard to the devices of Section A, any metal used in devices of this group of embodiment are preferably magnetic resonance imaging (MRI)-compatible metals, such as those discussed in Section A. In some embodiments, the materials used for the devices are radioopaque to facilitate using image guidance to place the devices.

C. Placement of the Devices of Sections A and B

The devices described in Sections A and B are preferably implanted using minimally invasive procedures. Typically, a trocar is placed through the scalp and other tools are then utilized inside the trocar to reduce contact with skin, thereby reducing the chance of infection. A hole is drilled in the skull, typically with a twist drill, with care being taken to protect underlying meninges. In embodiments which use a skull port piece, and in which the skull port piece is screwed into the calvarium, threads are created by a tap and the skull port then screwed in. In these embodiments, the device body is then passed through the lumen of the skull port piece. If the body is introduced in a compressed form over a balloon on a guide wire, the body is placed in position and the balloon slowly inflated to reduce tearing of the parenchyma that might result from rapid expansion. The balloon is then deflated and the guide wire and deflated balloon are withdrawn through the skull port piece. If the body is made of memory metal or other material with shape memory, the body is placed in position and expanded by exploiting the memory properties of the material. Once the device is in position and the body expanded, the reservoir is positioned in the skull port piece and any locking ring or other locking device engaged to secure the reservoir.

In embodiments not employing a skull port piece, such as the embodiments discussed in section A, above, after the hold is drilled in the skull, as described in the preceding paragraph, and the device is introduced into the organ parenchyma in a collapsed or compressed state. If the body is introduced in a compressed form over a balloon on a guide wire, the body is placed in position and the balloon slowly inflated to reduce tearing of the parenchyma that might result from rapid expansion. The balloon is then deflated and the guide wire and deflated balloon are withdrawn through the skull port. If the body is made of memory metal or other material with shape memory, the body is placed in position and expanded by exploiting the memory properties of the material.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A system for transferring fluid from a patient's brain, said system comprising:
   (a) a skull port piece having a lumen, and
   (b) a device having a tubular body with a longitudinal axis, which body has
      (i) a first section having a first end and a second end at opposite ends of said longitudinal axis and a transverse axis expandable from a first diameter to a second, larger diameter,
      (ii) a second section extending from said first section along said longitudinal axis, and having a first end and a second end having respective diameters, wherein (A) said first end of said second section is connected to said second end of said first section of said body and has a diameter larger than that of the diameter of said second end of said second section, and (B) said second end of said second section is adapted to be received into said lumen of said skull port piece, to lock said device to said skull port piece, or both, and
      (iii) a lumen extending through said device and disposed so that when said second end of said second section is received into said skull port piece or locked thereto or both, said lumen of said device is fluidly connected to said lumen of said skull port piece.

2. The system of claim 1, further wherein said skull port piece is circular.

3. The system of claim 1, further wherein said skull port piece has an internal lip surrounding the lumen.

4. The system of claim 1, further wherein said skull port piece has an external helical ridge.

5. The system of claim 1, further wherein said skull port piece lumen has a helical ridge.

6. The system of claim 3, further wherein the second end of the second section has extensions that can be pressed against the internal lip of the skull port piece.

7. The system of claim 1, further comprising a reservoir fluidly connected to said skull port piece.

8. The system of claim 7, wherein said reservoir is of silicon.

9. The system of claim 7, wherein said reservoir has a port.

10. The system of claim 7, further wherein the skull port piece has an internal lip surrounding the lumen and the reservoir has a rim sized to the lip of the skull port piece.

11. The system of claim 10, further comprising a locking ring that compresses the reservoir rim against the lip of the skull port piece.

12. The system of claim 11, further wherein the second end of the second section has tines, prongs or other extensions, which tines, prongs or other extensions are held in place against the lip of the skull port piece by the reservoir rim and locking ring.

13. The system of claim 1, wherein at least a portion of said body comprises a self-expanding material.

14. The system of claim 1, wherein said device is radioopaque.

15. The system of claim 1, further comprising a valve.

16. The system of claim 1, wherein said second end of said second section is adapted to be received into said skull port piece.

17. The system of claim 16, further wherein said second end of said second section has one or more tines, prongs or other extensions.

18. The system of claim 1, wherein said locking is releasable.

19. The system of claim 1, further wherein said second end of said second section has a helical ridge or tines, prongs or other extensions.

20. The system of claim 1, wherein said second end of said second section is adapted to be received into said lumen of said skull port piece.

21. The system of claim 20, wherein said second end of said second section is adapted to lock to said skull port piece.

22. The system of claim 20, further comprising a reservoir fluidly connected to said skull port piece.

23. The system of claim 1, wherein said second end of said second section is adapted to lock to said skull port piece.

24. The system of claim 23, wherein said locking is releasable.

25. The system of claim 23, further comprising a reservoir fluidly connected to said skull port piece.

\* \* \* \* \*